(12) United States Patent
Gullapalli

(10) Patent No.: US 6,251,426 B1
(45) Date of Patent: Jun. 26, 2001

(54) IBUPROFEN-CONTAINING SOFTGELS

(75) Inventor: Rampurna Prasad Gullapalli, Greensboro, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 0 days.

(21) Appl. No.: 09/389,003

(22) Filed: Sep. 2, 1999

(51) Int. Cl.[7] .............................. A61K 9/48; A61K 9/66; A61K 9/64; A61K 9/58
(52) U.S. Cl. .......................... 424/451; 424/452; 424/455; 424/456; 424/462; 514/772.5
(58) Field of Search ..................... 424/455, 456, 424/451, 452; 514/570, 629, 960, 772.8

(56) References Cited

U.S. PATENT DOCUMENTS

| | | | |
|---|---|---|---|
| 4,690,823 | * 9/1987 | Lohner et al. | 424/456 |
| 4,744,988 | * 12/1991 | Brox | 424/456 |
| 4,780,316 | * 10/1988 | Brox | 424/456 |
| 5,006,595 | 4/1991 | Smith et al. | 524/548 |
| 5,071,643 | * 12/1991 | Yu et al. | 514/570 |
| 5,141,961 | * 8/1992 | Coapman | 514/629 |
| 5,360,615 | 11/1994 | Yu et al. | 424/455 |
| 5,376,688 | 12/1994 | Morton et al. | 514/786 |
| 5,431,916 | 7/1995 | White | 424/451 |
| 5,468,502 | 11/1995 | Argiriadi et al. | 424/456 |
| 5,484,606 | 1/1996 | Dhabhar | 424/455 |
| 5,510,385 | 4/1996 | Stroppolo et al. | 514/555 |
| 5,538,737 | 7/1996 | Leonard et al. | 424/451 |
| 5,641,512 | 6/1997 | Cimiluca | 424/455 |
| 5,660,859 | 8/1997 | Cody et al. | 424/451 |
| 5,827,852 | 10/1998 | Russell et al. | 514/255 |

FOREIGN PATENT DOCUMENTS

| | | | |
|---|---|---|---|
| WO 95/19759 | 7/1995 | (WO) | A61K/47/10 |
| WO 00/30619 | 6/2000 | (WO) | A61K/9/48 |

* cited by examiner

Primary Examiner—Thurman K. Page
Assistant Examiner—Isis Ghali
(74) Attorney, Agent, or Firm—Rhodes & Mason, P.L.L.C.

(57) ABSTRACT

Liquid softgel fill formulations containing ibuprofen in free acid form, and softgel capsules comprised of a gelatin sheath enclosing such fill formulations, are prepared by dissolving more than 30% of ibuprofen in free acid form in polyethylene glycol and at least 10% by weight of a polyvinylpyrrolidone having an average molecular weight of from about 2,000 to about 54,000. The formulations may also include a surfactant to increase the bioavailability of the ibuprofen.

26 Claims, No Drawings

IBUPROFEN-CONTAINING SOFTGELS

BACKGROUND OF THE INVENTION

(1) Field of the Invention

The present invention relates generally to softgels or soft gelatin capsules and fill compositions therefor, and in particular to a soft gelatin capsule that contains a highly concentrated solution of ibuprofen in its free form.

(2) Description of the Prior Art

U.S. Pat. No. 4,690,823 to Lohner et al. describes a process for manufacturing ibuprofen-containing soft gelatin capsules in which up to 30 parts by weight of ibuprofen in free form is dissolved in from 70 to 85 parts by weight of polyoxyethylene-polyoxypropylene polymer or in a mixture of from 30 to 76 parts by weight of a polyalkylene glycol and from 7 to 40 parts by weight of a surfactant having a very rapid and high bio-availability of the active ingredient. Preferred suitable surfactants include, for example, polyoxyethyleneglycerol trihydroxystearate, polyoxyethylene $(C_{12-18})$-fatty alcohol ethers, polyoxyethylene stearate, polyoxyethylenesorbitan mono($C_{12-18}$)-fatty acid esters, and polyoxyethylene-polyoxypropylene polymer.

In the Lohner et al. process, up to 30 parts by weight of free form ibuprofen is dissolved by heating the free form ibuprofen with the selected solvent at a temperature of 45° to 60° C. If a concentration of ibuprofen greater than the maximum 30 parts by weight possible in solution is desired, up to 40 parts additional parts by weight of ibuprofen may also be suspended in the fill.

Softgel fills containing high concentrations of ibuprofen as a mixture of ibuprofen in free form and its salts are described in U.S. Pat. Nos. 5,071,643 and 5,360,615 to Yu et al. These fill formulations may be liquid, semi-solid or solid, and are formed by mixing 40–80% by weight ibuprofen, 0.1–1.5 moles of hydroxide ion per mole of ibuprofen, 1–20% by weight water, and 4–12% by weight glycerine or propylene glycol in polyethylene glycol. Solubility of the ibuprofen salts is further enhanced 2–10% by the further addition of 3–10% by weight of glycerin, or propylene glycol or 1–20% by weight of polyvinylpyrrolidone.

The preferred average molecular weight of the polyvinylpyrrolidone is 10,000–100,000. Higher percentages of above 5% polyvinylpyrrolidone, and higher molecular weight polyvinylpyrrolidone are used to prepare semi-solid and solid formulations for suppositiories, two piece capsules, and tablets.

Upon mixing under the conditions described by Yu et al., the polyethylene glycol acts to dissolve the free form of the ibuprofen; the hydroxyl ions source, e.g., sodium hydroxide or potassium hydroxide, partially forms an ibuprofen salt, and the water forms a solvation sphere around the acid salt permitting it to go into solution in the polyethylene glycol.

While softgel fill compositions containing ibuprofen salts can be produced by the above procedures, there is still a need for liquid softgel fill formulations with high concentrations, i.e., greater than 30% by weight, of ibuprofen in solution in its free acid form. In particular, there is a need for highly concentrated solutions containing ibuprofen in its free form that do not adversely affect the softgel capsules over an extended period of time.

SUMMARY OF THE INVENTION

The present invention relates to a liquid softgel fill formulation comprising greater than 30% by weight ibuprofen in free acid form in solution; from about 30 to about 60% by weight polyethylene glycol; and from about 10 to about 30% by weight of polyvinylpyrrolidone.

More specifically, liquid softgel fill formulations containing ibuprofen in free acid form, and softgel capsules comprised of a gelatin sheath enclosing such fill formulations, are prepared by dissolving more than 30% of ibuprofen in free acid form in polyethylene glycol and at least 10% by weight of a polyvinylpyrrolidone having an average molecular weight of from about 2,000 to about 54,000. The formulations may also include a surfactant to increase the bioavailability of the ibuprofen.

DETAILED DESCRIPTION OF THE INVENTION

The present invention relates to softgel fill formulations containing high concentrations, i.e., greater than 30% by weight of ibuprofen in its free acid form, and in particular to highly concentrated, preferably non-aqueous, ibuprofen fill formulations. Such formulations, when encapsulated into soft gelatin one-piece capsule sheaths by known techniques, provide long term stability, while still being of an acceptable size to the consumer. When used in the following description, "ibuprofen" will be understood to mean ibuprofen in its free acid form.

It has been found that these formulations can be prepared by dissolving ibuprofen in a solvent comprised of polyethylene glycol and polyvinylpyrrolidone, with each of the solvent components being present in a defined amount in the composition, and with each component having defined characteristics. Preferably, the formulation also includes a surfactant to enhance bioavailability of the ibuprofen.

Specifically, the formulations of the present invention are comprised of greater than 30% and up to 40% or more by weight ibuprofen, from 30 to 60% by weight polyethylene glycol, and from 10 to 30% by weight of polyvinylpyrrolidone. Preferably, the formulations are comprised of from 35 to 40% by weight ibuprofen, from 30 to 50% by weight polyethylene glycol, and from 15 to 30% by weight of polyvinylpyrrolidone.

It will be understood that the percentages of the above ingredients in a given formulation, which may also have other ingredients present, will be adjusted to total 100%. For example, up to 6% of a nasal decongestant, such as pseudoephedrine hydrochloride, or up to 10% of an antihistaminic, such as diphenhydramine hydrochloride, may be included in the formulation.

The preferred embodiments of the invention also contain at least about 10%, preferably from about 1% to about 10% by weight of a surfactant. Preferably, the surfactants are characterized by the capability to enhance the bioavailability of the ibuprofen, while being miscible with polyethylene glycol to form a clear solution. Suitable surfactants include esters of d-alpha tocopheryl, polyoxyethylene castor oil derivatives, and polyglycolyzed glycerides. Polyoxyethylene castor oil derivatives are the reaction products of ethylene oxide and castor oil or hydrogenated castor oil sold, for example, as Cremophors by BASF. Suitable polyglycolyzed glycerides are sold under the trademark Gelucire by Etablissements Gattefosse. An especially preferred surfactant is d-alpha tocopheryl polyethylene glycol 1000 succinate sold by Eastman Chemical Company under the trademark Vitamin E TPGS.

The polyethylene glycol component of the formulation should have an average molecular weight of up to about 1,000 in order to provide a liquid fill formulation. Preferably, the polyethylene glycol has an average molecular weight of at least about 200, with an average molecular weight of from about 400 to about 1,000 being preferred. PEG 600 is especially preferred.

The average molecular weight of the polyvinylpyrrolidone used in the present formulations may be in the range of from 2,000 to 54,000, but preferably is in the range of from about 2,000 to about 10,000. Preferred polyvinylpyrrolidones are sold under the trademarks Kollidon 12 PF and Kollidon 17 PF by BASF. These lower molecular weight polyvinylpyrrolidones have approximate molecular weights of 2,500 and 10,000 respectively. Another suitable polyvinylpyrrolidone is sold under the trademark Plasdone C-15 by ISP, and has a molecular weight of about 8,000. Unlike Yu, the present invention employs larger amounts of lower molecular weight polyvinylpyrrolidones to ensure that a liquid fill is obtained.

An additional advantage of these higher amounts of polyvinylpyrrolidone is the apparent reduction in the esterification reaction between the ibuprofen and the polyethylene glycol, a known disadvantage of mixing these two ingredients that results in the reduction of available ibuprofen in its free acid form. Use of the higher percentages of polyvinylpyrrolidone permits a corresponding reduction in the amount of polyethylene glycol required.

The fill formulations may be prepared by heating the polyethylene glycol and surfactant to 55±5° C., while mixing. The ibuprofen and polyvinylpyrrolidone are added and dissolved during heating and mixing. The procedure is carried out under a nitrogen atmosphere, and the final formulation is deaerated.

The fill formulation is encapsulated into one-piece gelatin sheath or shell that includes a plasticizer to control the softness and flexibility of the sheath, water, and optionally, other additives, such as flavorants, colorants, opacifiers, etc. The softgel capsules may be produced in a known manner with a rotary die process in which a molten mass of a gelatin sheath formulation is fed from a reservoir onto drums to form two spaced sheets or ribbons of gelatin in a semi-molten state. These ribbons are fed around rollers and brought together at a convergent angle into the nip of a pair of roller dies that include opposed die cavities. A fill formulation to be encapsulated is fed into the wedge-shaped joinder of the ribbons.

The gelatin ribbons are continuously conveyed between the dies, with portions of the fill formulation being trapped between the sheets inside the die cavities. The sheets are then pressed together, and severed around each die so that opposed edges of the sheets flow together to form a continuous gelatin sheath around the entrapped medicament. The part of the gelatin sheet that is severed from the segments forming the capsules is then collected for recycling, and the soft capsules are dried.

Various sheath formulations known in the prior art may be used to encapsulate the fill formulations of the present invention. For example, suitable sheath formulations may include from about 35 to about 50% by weight gelatin; at least 20% by weight, and preferably up to about 40% by weight, of a plasticizer; and from about 25 to about 50% by weight water. These formulations, when formed into capsules and dried, will result in capsule sheaths comprised of from about 45 to about 75% by weight gelatin; from about 20% to about 40% by weight plasticizer; and from about 5 to about 15% by weight water.

The gelatin will normally have a bloom in the range of from about 150 to about 275, and may be Type A or B gelatins or a mixture thereof. Limed bone, acid bone, fish and/or pig skin gelatins may be used.

The sheath plasticizer preferably is sorbitol, sorbitol special (a mixture of sorbitol and sorbitan), maltitol, or a mixture thereof While glycerin can be used as a plasticizer, it has been found that the ibuprofen may esterify with the glycerin, reducing the amount of available free form ibuprofen. Therefore, the non-glycerin plasticizers are preferred.

The sheath formulations may also contain other ingredients, such as taste modifiers, coloring agents, and moisture retaining agents. Taste modifiers include non-reducing sugars, such as xylitol, maltitol, or Lycasin® manufactured by Roquette America, Inc. of Keokuk, Iowa and normally will comprise up to about 5% by weight of the sheath composition. Suitable moisture retaining agents include celluloses, cellulose derivatives, starches, starch derivatives, vegetable gums, non-hygroscopic, mono-, di- and oligosaccharides, and silicon dioxide. Various FD&C coloring agents may be used to impart the desired color to the capsule.

In order to be acceptable to the consumer, the softgel capsule should be of a size that is easily swallowed. Generally, the fill size of the capsule will be less than 600 mg, and preferably about 500 mg or less, for the capsule to be of an acceptably small dimension. The required effective dosage of ibuprofen will normally be at least 175 mg, and preferably about 200 mg. Therefore, the preferred capsules will contain at least about 35% by weight of ibuprofen. The overall volume of the fill is also made possible by the fact that only polyethylene glycol and polyvinylpyrrolidone are required for dissolution, with a surfactant preferably being included to enhance bioavailability of the ibuprofen when ingested. Thus, the compositions may be free of water and other ingredients that increase the fill volume.

The following examples are for the purpose of illustrating the present fill formulation, and softgels comprised of these fill formulation, and are not to be taken as in any way limiting the scope of the invention. Examples 1–10 are representative fill formulations containing in excess of 30% by wt. ibuprofen in its free acid form. Examples 11–13 are representative sheath formulations used to encapsulate the fill formulations of Examples 1–10.

Example 1

| Fill Ingredients | % by wt. |
|---|---|
| Ibuprofen | 35 |
| PEG 600 | 37 |
| Kollidon 17 PF | 22 |
| Vitamin E TPGS | 6 |

Example 2

| Fill Ingredients | % by wt. |
|---|---|
| Ibuprofen | 35 |
| PEG 600 | 35 |
| Kollidon 17 PF | 20 |
| Vitamin E TPGS | 5 |
| Water, purified | 5 |

Example 3

| Fill Ingredients | % by wt. |
| --- | --- |
| Ibuprofen | 37 |
| PEG 600 | 37 |
| Kollidon 17 | 20 |
| Vitamin E TPGS | 6 |

Example 4

| Fill Ingredients | % by wt. |
| --- | --- |
| Ibuprofen | 35 |
| PEG 600 | 40 |
| Kollidon 30 | 15 |
| Cremophor RH 40 | 5 |
| Propylene glycol | 5 |

Example 5

| Fill Ingredients | % by wt. |
| --- | --- |
| Ibuprofen | 35 |
| PEG 600 | 33 |
| Kollidon 17 PF | 22 |
| Gelucire 44/14 | 10 |

Example 6

| Fill Ingredients | % by wt. |
| --- | --- |
| Ibuprofen | 35 |
| PEG 600 | 40 |
| Kollidon 30 | 15 |
| Cremophor RH 60 | 5 |
| Propylene glycol | 5 |

Example 7

| Fill Ingredients | % by wt. |
| --- | --- |
| Ibuprofen | 35 |
| PEG 600 | 35 |
| Kollidon 30 | 15 |
| Cremophor RH 60 | 10 |
| Propylene glycol | 5 |

Example 8

| Fill Ingredients | % by wt. |
| --- | --- |
| Ibuprofen | 40 |
| PEG 600 | 40 |
| Kollidon 17 PF | 20 |

Example 9

| Fill Ingredients | % by wt. |
| --- | --- |
| Ibuprofen | 40 |
| PEG 600 | 40 |
| Kollidon 17 PF | 15 |
| Vitamin E TPGS | 5 |

Example 10

| Fill Ingredients | % by wt. |
| --- | --- |
| Ibuprofen | 40 |
| PEG 600 | 30 |
| Kollidon 17 PF | 25 |
| Vitamin E TPGS | 5 |

Example 11

| Sheath Ingredients | % by wt. |
| --- | --- |
| Gelatin, lime bone | 42 |
| Sorbitol, special | 9 |
| Maltitol, 75% | 12 |
| Water, purified | 37 |

Example 12

| Sheath Ingredients | % by wt. |
| --- | --- |
| Gelatin, lime bone | 42 |
| Sorbitol, special | 15 |
| Maltitol, 75% | 6 |
| Water, purified | 37 |

Example 13

| Sheath Ingredients | % by wt. |
| --- | --- |
| Gelatin, lime bone | 42 |
| Glycerin | 8 |
| Maltitol, 75% | 12 |
| Water, purified | 38 |

Certain modifications and improvements will occur to those skilled in the art upon a reading of the foregoing description. It should be understood that all such modifications and improvements have been deleted herein for the sake of conciseness and readability but are properly within the scope of the follow claims.

What is claimed is:

1. A liquid softgel fill formulation consisting essentially of:
    a) greater than 30% by weight ibuprofen in free acid form in solution;
    b) from about 30 to about 60% by weight polyethylene glycol;
    c) from about 10 to about 30% by weight of polyvinylpyrrolidone; and
    d) from about 1 to about 10% by weight of a surfactant.

2. The softgel fill formulation of claim 1, wherein said ibuprofen is present in an amount of at least about 35% by weight.

3. The softgel formulation of claim 1, wherein said polyethylene glycol has an average molecular weight of from about 200 to about 1,000.

4. The softgel formulation of claim 1, wherein said polyvinylpyrrolidone has an average molecular weight of from about 2,000 to about 54,000.

5. The softgel fill formulation of claim 1, further including up to about 6% of a nasal decongestant or up to about 10% of an antihistaminic.

6. The softgel fill formulation of claim 1, further including up to about 10% by weight of a surfactant to increase the bioavailability of said ibuprofen.

7. The softgel formulation of claim 1, wherein said surfactant is selected from the group consisting of esters of d-alpha-tocopheryl, polyoxyethylene castor oil derivatives, and polyglycolyzed glycerides.

8. A liquid softgel fill formulation consisting essentially of:
   a) greater than 30% by weight ibuprofen in free acid form in solution;
   b) from about 30 to about 60% by weight of polyethylene glycol having an average molecular weight of from about 200 to about 1,000;
   c) from about 10 to about 30% by weight of polyvinylpyrrolidone having an average molecular weight of from about 2,000 to about 54,000; and
   d) from about 1 to about 10% by weight of a surfactant to increase the bioavailability of said ibuprofen.

9. The softgel fill formulation of claim 8, wherein said polyethylene glycol is has an average molecular weight of about 600.

10. The softgel formulation of claim 8, wherein said surfactant is selected from esters of d-alpha tocopheryl, polyoxyethylene castor oil derivatives, and polyglycolyzed glycerides.

11. A softgel capsule comprised of a sheath enclosing a liquid fill, said fill consisting essentially of:
   a) greater than 30% by weight ibuprofen in free acid form in solution;
   b) from about 30 to about 60% by weight polyethylene glycol;
   c) from about 10 to about 30% by weight polyvinylpyrrolidone; and
   d) from about 1 to about 10% by weight of a surfactant.

12. The softgel capsule of claim 11, wherein said ibuprofen is present in an amount of from about 35% to about 40% by weight of said fill.

13. The softgel capsule of claim 11, wherein said polyethylene glycol has an average molecular weight of from about 200 to about 1,000.

14. The softgel capsule of claim 11, wherein said surfactant is selected from esters of d-alpha tocopheryl, polyoxyethylene castor oil derivatives, and polyglycolyzed glycerides.

15. The softgel capsule of claim 11, wherein said polyvinylpyrrolidone has an average molecular weight of from about 2,000 to about 11,000.

16. The softgel capsule of claim 11, wherein said sheath is comprised of from about 45 to about 75% by weight gelatin, from about 20 to about 40% by weight of a plasticizer, and from about 5 to about 15% by weight water.

17. The softgel capsule of claim 11, further including up to about 6% of a nasal decongestant or up to about 10% of an antihistaminic.

18. A softgel capsule comprised of a sheath enclosing a liquid fill, said fill consisting essentially of:
   a) at least 35% by weight ibuprofen in free acid form in solution;
   b) from about 30 to about 50% by weight polyethylene glycol having an average molecular weight of from about 200 to about 1,000;
   c) from about 15 to about 30% by weight of polyvinylpyrrolidone having an average molecular weight of from about 2,000 to about 11,000; and
   d) a surfactant to increase the bioavailability of said ibuprofen.

19. The softgel capsule of claim 18, wherein said surfactant is selected from esters of d-alpha tocopheryl, polyoxyethylene castor oil derivatives, and polyglycolyzed glycerides.

20. The softgel capsule of claim 18, wherein said sheath is comprised of from about 45 to about 75% by weight gelatin, from about 20 to about 40% by weight plasticizer, and from about 5 to about 15% by weight water.

21. The capsule of claim 20, wherein said sheath plasticizer is selected from the group consisting of sorbitol, sorbitol special, maltitol, and mixtures thereof.

22. The capsule of claim 18, wherein the total weight of said capsule fill is less than 600 mg., and the weight of said ibuprofen is at least 200 mg.

23. A liquid softgel fill formulation consisting essentially of:
   a) greater than 30% by weight ibuprofen in free acid form in solution;
   b) from about 30 to about 60% by weight polyethylene glycol;
   d) from about 10 to about 30% by weight of polyvinylpyrrolidone, wherein the ratio of polyethylene glycol to polyvinylpyrrolidone less than about 2.5:1; and
   d) a surfactant to increase the bioavailability of said ibuprofen.

24. The liquid softgel fill formulation of claim 23 wherein the ratio of polyethylene glycol to polyvinylpyrrolidone is between about 1.6:1 and about 1.8:1.

25. A softgel capsule comprised of a sheath enclosing a liquid fill, said fill consisting essentially of:
   a) greater than 30% by weight ibuprofen in free acid form in solution;
   b) from about 30 to about 60% by weight polyethylene glycol;
   c) from about 10 to about 30% by weight polyvinylpyrrolidone, wherein the ratio of polyethylene glycol to polyvinylpyrrolidone is less than about 2.5:1; and
   d) a surfactant to increase the bioavailability of said ibuprofen.

26. The softgel capsule of claim 25 wherein the ratio of polyethylene glycol to polyvinylpyrrolidone is between about 1.6:1 and about 1.8:1.

* * * * *